United States Patent [19]
Grabley et al.

[11] Patent Number: 5,128,370
[45] Date of Patent: Jul. 7, 1992

[54] FURANS AND LACTONES FROM STREPTOMYCETES AND THE USE THEREOF

[75] Inventors: Susanne Grabley, Königstein/Taunus; Joachim Wink, Offenbach; Klaus Kühlein, Kelkheim; Gerhard Seibert, Darmstadt; Klaus Hütter, Bad Soden am Taunus; Hermann Uhr, Leverkusen; Axel Zeeck, Göttingen, all of Fed. Rep. of Germany

[73] Assignee: Hoechst Aktiengesellschaft, Frankfurt am Main, Fed. Rep. of Germany

[21] Appl. No.: 325,810

[22] Filed: Mar. 20, 1989

[30] Foreign Application Priority Data

Mar. 22, 1988 [DE] Fed. Rep. of Germany ....... 3809562

[51] Int. Cl.$^5$ .................... A61K 31/34; C07D 307/12; C07D 307/28; C07D 307/44
[52] U.S. Cl. .................................. 514/461; 514/473; 549/295; 549/313; 549/323; 549/429; 549/475; 549/479; 549/497; 549/502; 549/506; 549/507; 435/254
[58] Field of Search ................. 549/497, 502; 514/461

[56] References Cited

PUBLICATIONS

Helv. Chim. Acta 26:216–228 (1958).
Bogner et al., "Etude conformationnelle de tetrahydrofurannes methyles," Bulletin de la Societe Chimique de France, No. 9, pp. 3216–3524, (1972).
Yoshida, et al., "Concurrent Anodic Cyanation and Methoxylation of Methylated Furans, Oxidation Potential and Reactivity, and Stereochemical Control of Addition," Bulleting of the Chemical Society of Japan, No. 1, pp. 229–240, (1987).
Zamojski, et al., "Synthesis of 3–Substituted Furans," Journal of Organic Chemistry, vol. 402, No. 6, pp. 1089–1090 (1977).
Davies, et al., "Chiral Discrimination in the Reactions of the Enolate," Tetrahedron Letters, Band 26, No. 39, pp. 4815–4818, (1985).
Alper, et al., "Palladium–catalysed conversion of Alkenols into Five– and Six–membered Ring Lactones at Room Temperature and Atmospheric Pressure," Journal of the Chemical Society, Chemical Communications, pp. 511–512, (1985).
Matsuda, et al., "A Simple Synthesis of α-Ylidene γ-Lactones from γ-Trimethylsiloxy Nitriles," Bulletin of the Chemical Society of Japan, vol. 52, No. 8, pp. 2389–2393, (1979).
Ikariya, et al., "Regioselective Hydrogenation of Unsymmetrically Substituted Cyclic Anhydrides Catalyzed by Ruthenium Complexes with Phosphine Ligands," Bulletin of the Chemical Society of Japan, vol. 57, No. 3, pp. 897–898, (1984).
Mukaiyama, et al., "Convenient Synthesis of the Antibiotic Botryodiplodin," Chemical Abstracts, vol. 82, No. 7, p. 412, (1974).
Dunlop et al., The Furans, ACS Monograph Series (1953).
Noyce et al., J. Org. Chem., vol. 37 (1972) pp. 2620–2623.
Summers et al., Chemical Abstracts, vol. 111 (1989) 214382k.

Primary Examiner—Richard L. Raymond
Attorney, Agent, or Firm—Finnegan, Henderson, Farabow, Garrett and Dunner

[57] ABSTRACT

New furans and lactones from streptomycetes, a process for the preparation thereof, and the use thereof.

It is possible with the aid of various streptomycetes species to prepared new compounds having a furan or lactone structure. These compounds have a pharmacological, especially antibiotic, action.

3 Claims, No Drawings

FURANS AND LACTONES FROM STREPTOMYCETES AND THE USE THEREOF

H. Zähner has described the preparation, with the aid of Streptomyces ramulosus sp. nov., of the keto acetoxylactone acetomycin which has antimicrobial activity [Helvetica Chimica Acta 26. 216 (1958)].

It has now been found, surprisingly, that Streptomyces spec. DSM 4349, DSM 4355, DSM 4200 and DSM 4211 synthesize new furans and lactones having a pharmacological, in particular antibacterial, action, and intermediates which contain rhamnose and from which the sugar can easily be obtained.

Thus the invention relates to:

1. A compound of the general formula I,

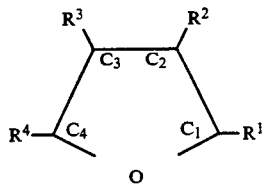

in which, independently of one another, $R_1$ can be hydrogen or an oxo group, $R_2$ can be methyl or 1-hydroxyethyl, $R_3$ can be hydrogen, methyl or rhamnosyloxycarbonyl, and $R_4$ can be hydrogen, 2-hydroxypropyl, acetoxy or methyl, it being possible for the bonds between $C_1$ and $C_2$, and $C_3$ and $C_4$, to be double bonds.

2. A process for the preparation of the compound of the general formula I, which comprises cultivating Streptomyces spec. DSM 4349, DSM 4355, DSM 4200 and DSM 4211, as well as the variants and mutants thereof, each individually or combined in a mixed culture, in a nutrient medium until the compound of the formula I accumulates in the culture.

3. The use of the compound characterized under 1. for the preparation of rhamnose or for the preparation of medicines, especially having antibiotic activity.

The compound is described in detail hereinafter, especially in its preferred embodiments. The invention is furthermore defined in the patent claims.

The Streptomycetes used according to the invention were isolated from soil samples and have been deposited at the Deutsche Sammlung von Mikroorganismen under the stated DSM numbers. The deposition took place in accordance with the rules of the Budapest treaty on Aug. 5, 1987, Aug. 13, 1987 and Jan. 15, 1988. The descriptions of the microorganisms are as follows:

|  | DSM 4349 | DSM 4355 | DSM 4200 | DSM 4211 |
| --- | --- | --- | --- | --- |
| Spore color: | blue/gray | pink | red/brown | yellow |
| Spore chain: | divergent spiral | straight | compact spiral | compact spiral |
| Spore surface: | spiky | — | smooth | — |
| Melanin: Pigment | + | + | — | — |
| Substrate mycelium | Endo: — Exo: — | Endo: — Exo: — | Endo: — Exo: red | Endo: — Exo: red |
| Aerial mycelium | Endo: — | Endo: — | Endo: brown | Endo: — |
| Utilization of sugars and sugar alcohols | Exo: — Arabinose Xylose Rhamnose Raffinose Mannitol | Exo: — not tested | Exo: — Arabinose Xylose | Exo: — Not tested |
| Acid utilization: | Oxalate Malonate | not tested | — | not tested |

In a nutrient solution which contains a carbon source and a nitrogen source as well as the customary inorganic salts, Streptomyces spec. DSM 4349, DSM 4355, DSM 4200 and DSM 4211 produce, individually or combined in a mixed culture, the abovementioned compound of the general formula I, in which $R^1$ to $R^4$ have the abovementioned meaning, and the bonds between $C_1$ and $C_2$, and $C_3$ and $C_4$, can be double bonds.

DSM 4349 preferentially synthesizes the compound of the general formula I in which $R^1$ and $R^3$ denote hydrogen, $R^2$ denotes methyl and $R^4$ denotes 2-hydroxypropyl, with the bonds between $C_1$ and $C_2$, and $C_3$ and $C_4$, being double bonds, whereas DSM 4200 and DSM 4211 preferentially produce the compounds in which $R^1$ denotes an oxo group, $R^2$ denotes 1-hydroxyethyl, $R^3$ denotes methyl and $R^4$ denotes hydrogen or acetoxy, as well as the compound in which $R^1$ is hydrogen, $R^2$ and $R^4$ are methyl, and $R^3$ is rhamnosyloxy-carbonyl, with the bonds between $C_1$ and $C_2$, and $C_3$ and $C_4$, being double bonds. It is possible with the aid of DSM 4355 to prepare each of the said compounds.

It is also possible, in place of the said DSM strains, to use the mutants and variants thereof, as long as they synthesize at least one of these compounds. Such mutants can be generated in a manner known per se by physical means, for example irradiation such as with ultraviolet or X-rays, or chemical mutagens such as, for example, ethyl methanesulfonate (EMS), N-methyl-N'-nitro-N-nitrosoguanidine (MNNG) or 2-hydroxy-4-methoxybenzophenone (MOB).

Suitable and preferred carbon sources for the aerobic fermentation are assimilable carbohydrates and sugar alcohols such as, for example, glucose, lactose or D-mannitol and glycerol, as well as carbohydrate-containing natural products such as malt extract. Suitable and preferred nitrogen-containing nutrients are: amino acids, peptides and proteins, as well as the degradation products thereof, such as peptones or tryptones, also meat extracts, milled seeds, for example of corn, wheat, beans, soybean or the cotton plant, distillation residues from the production of alcohol, meat meals or yeast extracts, as well as ammonium salts and nitrates. The nutrient solution can also contain, for example, chlorides, carbonates, sulfates or phosphates of the alkali metals or alkaline earth metals, iron, zinc and manganese as additional inorganic salts.

The production of the furans and lactones of the general formula I takes place especially well in a nutrient solution which contains glycerol in concentrations of 0.5 to 6%, preferably 2 to 4%, as well as casein peptone in concentrations of 0.1 to 4%, preferably 0.5 to 2%, in each case based on the weight of the complete nutrient solution. Other preferred nutrient media, especially for DSM 4355 to prepare the compounds in which $R^1$ denotes an oxo group, $R^2$ denotes 1-hydroxyethyl, $R^3$ denotes methyl and $R^4$ denotes hydrogen or acetoxy, are those which contain crushed oats in concentrations of 0.5 to 6%, preferably 1 to 3%, and soybean meal in concentrations of 0.1 to 3%, preferably 0.3 to 1%, and nutrient media which contain soybean meal and mannitol in concentrations of 0.5 to 6%, preferably 1 to 4%, likewise in each case based on the weight of the complete nutrient medium.

The fermentation is carried out aerobically, that is to say, for example, submerged with shaking or stirring in shaken flasks or fermenters, where appropriate passing in air or oxygen, The fermentation can take place in a temperature range of about 18° to 40° C., preferably at about 25° to 30° C., in particular at 28° to 30° C. The microorganism is cultivated under the stated conditions until the stationary phase is reached, for about 60 to 100 hours, preferably 70 to 75 hours. The fermentation takes place essentially in a pH range of about 6 to 8, or in the preferred range from 6.5 to 7.5.

The microorganisms are advantageously cultivated in several stages, i.e.. one or more precultures are initially prepared in a liquid nutrient medium and are then transferred into the actual production medium, the main culture, for example in the ratio 1 : 10 by volume. The preculture is obtained, for example, by transferring a sporulated mycelium into a nutrient solution and leaving it to grow for about 48 to 72 hours. The sporulated mycelium can be obtained by leaving the strain to grow for about 7 days on a solid or liquid nutrient medium, for example yeast/malt agar.

The progress of the fermentation can be monitored by means of the pH of the culture or of the mycelium volume, or by thin-layer chromatography or testing the biological activity.

During the fermentation of the said strains the levorotatory compound of the formula II

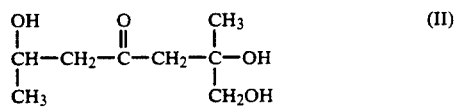

is produced as intermediate in optically pure form. The invention therefore also relates to this compound and to the use thereof as intermediate for the preparation of the compound of the general formula I in which $R^1$ and $R^3$ are hydrogen, $R^2$ is methyl and $R^4$ is 2-hydroxypropyl.

The furans and lactones of the general formula I, according to the invention, are isolated from the culture medium by known methods which take account of the chemical, physical and biological properties of the products. To test the antibiotic concentration in the culture medium or in the individual stages in the isolation, it is possible to use thin-layer chromatography, for example on silica gel with chloroform/methanol as mobile phase, expediently comparing the amount of antibiotics produced with a calibration solution.

The lactones and furans of the general formula I are present in the mycelium and in the culture broth. They can be extracted from the unfiltered culture broth using an organic solvent which is immiscible or only slightly miscible with water, such as chloroform or ethyl acetate. However, since only a small portion of them is present in the mycelium, it is advantageous to separate the culture broth from the mycelium, for example by centrifugation or filtration, preferably with the addition of filtration aids.

The compounds of the formula I can then be isolated from the supernatant or filtrate, expediently in the slightly acid to neutral pH range, preferably at pH 6 to 7. It is expedient to use for this purpose organic solvents which are slightly miscible or immiscible with water, especially chlorinated hydrocarbons such as chloroform or methylene chloride, or esters such as ethyl acetate, or acetone. Highly lipophilic constituents, which may comprise up to about 80% of the total extract, are removed from the extracts, where appropriate after evaporation and taking up in a polar organic solvent, by precipitation with a non-polar solvent, expediently a hydrocarbon such as petroleum ether. The lactones and furans can be isolated from the residue by chromatography.

For further isolation from the defatted crude extract, the latter is expediently purified on a silica gel column, mobile phases which have proven useful being mixtures of low molecular weight chlorinated hydrocarbons and alkanols, for example chloroform and methanol in the ratio 4 : 1 by volume or ethyl acetate and hexane in the ratio 1 : 2 by volume. The adsorbed components are eluted successively.

The customary processing steps can be used to isolate the pure substances, such as chromatography, gel filtration or precipitation from solutions thereof in suitable organic solvents. Chromatography on silica gel has proven particularly useful, using as mobile phase a mixture of ethyl acetate and hexane in a ratio of, for example, 1 : 2 by volume.

The levorotatory compound of the formula II in optically pure form can likewise be isolated in the way described above.

The lactones and furans are oily and readily soluble in methanol, acetone, DMSO, dioxane and chloroform, but not in water and alkanes. The substances are stable in the solid state as well as in solution in the pH range from 3 to 9, especially from 5 to 8, and can thus be incorporated in pharmaceutical formulations.

The antibacterial action is particularly evident against Staphylococci and Streptococci, as can be shown, for example, in the agar plate diffusion test in vitro (10 μl/test disk of diameter 6 mm). Various organisms which are sensitive to a minimal inhibitory concentration in the range from $>10$ to $<50$ μg/ml are, for example, *Staphylococcus aureus, Streptococcus pyogenes* and *Streptococcus faecium*.

EXAMPLES 1. a) Preparation of a suspension of spores of the producer strain:

100 ml of nutrient solution (4 g of yeast extract, 10 g of malt extract, 4 g of glucose, 1 l of tap water, pH before sterilization 7.3) in a 500 ml Erlenmeyer flask is inoculated with the strain DSM 4355 and incubated in a rotating shaker at 120 rpm and 27° C. for 72 hours. Then 20 ml of culture liquid are homogeneously distributed in a 500 ml Erlenmeyer flask containing the nutrient medium of the abovementioned composition, to which 20 g of agar/l have been added for solidification, and decanted off. The cultures are incubated at 27° C. for 10 to 14 days.

The spores which have been produced after this time in one flask are rinsed out with 500 ml of deionized water, which contains one drop of a commercially available nonionic surfactant (Triton×100, from Serva), and immediately used further or stored at −22° C.

An analogous procedure can be applied here and hereinafter to the strains DSM 4349, DSM 4200 and DSM 4211.

b) Preparation of a culture or preculture of the producer strain in an Erlenmeyer flask.

A 500 ml Erlenmeyer flask containing 100 ml of a nutrient solution of the composition 2% meat meal, 10% malt extract, 1% calcium carbonate and water ad 100 ml (pH 7.2 before autoclaving) is inoculated with a culture which has been cultivated in a slant tube or with 0.2 ml of spore suspension and is incubated in a shaker at 120 rpm and 27° C. The maximum antibiotic production is reached after 72 hours. A 48-hour old submerged culture (5%) from the same nutrient solution suffices to inoculate 10 and 100 l fermenters.

2. Preparation of the furans and lactones

A 10 l fermenter is operated under the following conditions:

| Nutrient medium: | 30 g/l glycerol |
| --- | --- |
| | 2 g/l casein peptone |
| | 1 g/l $K_2HPO_4$ |
| | 1 g/l NaCl |
| | 0.5 g/l $MgSO_4.7H_2O$ |
| | 5 ml/l trace element solution |
| Trace elements: | 3 g/l $CaCl_2.2H_2O$ |
| | 1 g/l $FeC_6O_7H_5$ |
| | 0.2 g/l $MnSO_4$ |
| | 0.1 g/l $ZnCl_2$ |
| | 0.025 g/l $CuSO_4.5H_2O$ |
| | 0.02 g/l $Na_2B_4O_7.10H_2O$ |
| | 0.004 g/l $CoCl_2$ |
| | 0.01 g/l $Na_2MoO_4.2H_2O$ |
| Incubation time: | 72 hours |
| Incubation temperature: | 30° C. |
| Stirrer speed: | 250 rpm |
| Aeration: | 4 l of air/min. |

Foam formation can be suppressed by repeated addition of a few drops of ethanolic polyol solution. The production maximum is reached after about 60-80 hours (pH =5.3). The yields are about 10 mg/l.

3. Isolation of the furans and lactones

After the fermentation, the culture broth is filtered with the addition of 2% Celite as filtration aid. The mycelium is extracted with acetone, the organic phase is evaporated, and the aqueous residue is extracted with ethyl acetate. The culture filtrate is likewise exhaustively extracted with ethyl acetate at pH 7. The latter extract is combined with that from the mycelium, and the mixture is dried and evaporated. The crude product is chromatographed on a silica gel column (silica gel 60, from Macherey-Nagel) with a mixture of ethyl acetate and hexane in the ratio 1 : 2 (v:v).

4. a) Characterization of the compound

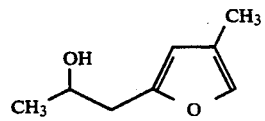

Thin-layer chromatography:

Silica gel 60 $F_{254}$: Chloroform/methanol (9 : 1, v:v): Rf 0.40

EI-MS (70 eV): m/e = 140 ($M^{30}$, 20%); 97 (100%) corresponding to $C_8H_{12}O_2$(140.18)

UV (Methanol): $\lambda_{max}$ ($\epsilon$) = 224 (3000) nm

UV (Methanol/HCl): $\lambda_{max}$ ($\epsilon$) = 218 (2700) nm

UV (Methanol/NaOH): $\lambda_{max}$ ($\epsilon$) = 219 (6400) nm $^1$H NMR (200 MHz, $CDCl_3$) : $\delta$ = 1.22 (d,3H,J = 6 Hz, 8-$H_3$); 2.00 (s,3H,9-$H_3$); 2.7 (m,2H,6-$H_2$); 3.7 (m,1H,7-H); 4.1 (m,1H, exchangeable, 7-OH); 6.00 (s,1H,3-H); 7.1 (s,1H,5-H) ppm.

b) Characterization of the compound:

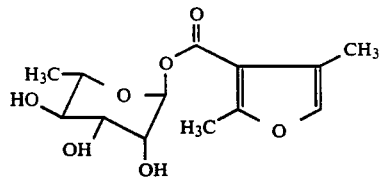

Thin-layer chromatography: Silica gel 60 $F_{254}$ Chloroform/methanol (9:1, v:v): Rf 0.28

EI-MS (70 eV): m/e = 286 ($M^+$, 10%, $C_{13}H_{18}O_7$, high resolution) 140 (74%, $C_7H_8O_3$, high resolution); 123 (100%, $C_7H_7O_2$, high resolution).

IR (KBR): 3200-3500, 2978, 2930, 1705, 1608 $cm^{-1}$.

$^1$H NMR (200 MHz, $CDCl_3$): $\delta$ = 1.28 (d,3H,J = 5.9 Hz,6'-$H_3$); 2.06 (d,3H,J<1 Hz, 7-$H_3$); 2.47 (s, 3H,6-$H_3$); 3.57 (t,1H, J = 9.4 Hz, 4'-H); 3.70 (dq,1H,J = 9.4/5.9 Hz, 5'-H); 3.81 (dd,1H,J = 9.4/3.4 Hz, 3'-H); 4.05 (dd,1H,J = 3.4/1.6 Hz, 2'-H); 6.20 (s,broad,1H'1 -H); 6.97 (s,1H,5-H) ppm.

$^{13}$C NMR (50.3 MHz, $CD_3OD$): $\delta$ = 10.6 q; 14.7 q; 18.1 q (C-6'); 71.3 d; 72.3 d; 72.6 d; 73.3 d; 95.1 d (C-1'); 113.9 s (C-4); 122.1 s (C-3); 139.6 d(C-5); 162.4 s (C-2); 163.9 s (C-8) ppm.

$[\alpha]_D^{20}$ : (c = 0.5, methanol) −30° c) Characterization of the compounds

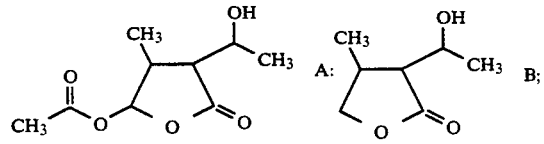

The compounds of the abovementioned formulae exist as a mixture in the ratio 2:1 (A:B)

Thin-layer chromatography:

Silicagel 60 $F_{254}$Chloroform/methanol (9:1,v:v): Rf. 0.57

IR (KBr): 3200-3600, 1785, 1760 $cm^{-1}$ $^1$H NMR (200 MHz, $CD_3OD$):

Signals for compound A: $\delta$ = 1.21 (d,3H,J = 7 Hz); 1.31 (d,3H,J = 6.6 Hz); 2.12 (s,3H,acetyl-$CH_3$); 2.50 (dd,1H,J = 10.2/3.3 Hz,3-H); 2.9 (m,1H,4-H); 4.28 (m,1H,6-H); 6.52 (d,1H,5-H) ppm.

Signals for compound B: $\delta$ = 1.20 (d,3H,J = 7 Hz); 1.30 (d,3H,J = 6.6 Hz); 2.26 (dd, 1H,J = 8/3.8 Hz, 3-H); 2.75 (m,1H,4-H); 3.80 (t,1H,J = 8 Hz, 5-$H_a$); 4.43 (t,1H,J = 8 Hz,5-$H_b$) ppm.

$^{13}$C NMR (50.3 MHz,$CD_3OD$):

Signals for compound A: $\delta$ = 14.1 g; 20.6 g; 21.9 g; 35.2 d; 52.2 d; 66.7 d; 96.3 d; 171.0 s; 178.4 s ppm.

Signals for compound B: $\delta$ = 19.1 g; 21.8 g; 31.5 d; 55.4 d; 67.2 d; 74.7 t; 180.9 s ppm.

d) Characterization of the compound II

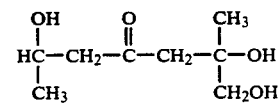

$C_8H_{16}O_4$(176.2)

Thin-layer chromatography: Silica gel 60 $F_{254}CHCl_3$/methanol (9:1, v:v): Rf = 0.23

$^1$H NMR (200 MHz, CDCl$_3$/CD$_3$OD): $\delta$ =1.15 (s,3H,8-H$_3$); 1.2 (d,3H,1-CH$_3$); 2.65 (d,1H,J =12.5 Hz,5-H$_b$); 2.7 (dd,3-H); 2.75 (d,1H,J =12.5 Hz,5-H$_a$); 3.85 (m,2H,7H$_2$); 4.2 (q,1H,2-H) ppm.

$^{13}$C NMR (50.3 MHz, CDCl$_3$/CD$_3$OD: $\delta$ =23.3 q (CH$_3$); 23.4 q (CH$_3$); 49.6 t (CH$_2$); 52.9 t (CH$_2$); 63.5 t (OCH$_2$); 68.7 d (CH); 72.1 d (CH); 211.2 s (CO) ppm.

Optical rotation [$\alpha$]: $-12°$ (c =1 in CHCl$_3$)

We claim:

1. A compound of the general formula I,

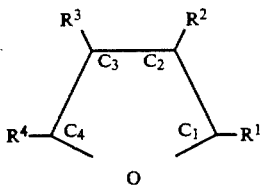

I in which, independently of one another,
- $R^1$ denotes hydrogen,
- $R^2$ denotes methyl or 1-hydroxyethyl,
- $R^3$ denotes hydrogen or methyl, and
- $R^4$ denotes hydrogen, 2-hydroxypropyl or methyl, it being possible for the bonds between $C_1$ and $C_2$, and $C_3$ and $C_4$, to be double bonds, with the proviso that:
- when $R^2$ is methyl, $R^4$ is 2-hydroxypropyl, and
- when $R^4$ is hydrogen or methyl, $R^2$ is hydroxyethyl.

2. A pharmaceutical composition, comprising an effective amount of a compound of the formula I as claimed in claim 1 together with a pharmaceutically acceptable carrier.

3. An antibiotic medicine, comprising an effective amount of a compound of the formula I as claimed in claim 1 together with a pharmaceutically acceptable carrier.

* * * * *

UNITED STATES PATENT AND TRADEMARK OFFICE
CERTIFICATE OF CORRECTION

PATENT NO. :    5,128,370
DATED      :    July 07, 1992
INVENTOR(S) :   Susanne Grabley et al.

It is certified that error appears in the above-identified patent and that said Letters Patent is hereby corrected as shown below:

Abstract, line 1, change "streptomycetes" to --Streptomycetes--.

Abstract, line 3, change "streptomycetes" to --Streptomycetes--.

Abstract, line 4, change "prepared" to --prepare--.

Signed and Sealed this

Fourth Day of January, 1994

Attest:

BRUCE LEHMAN

*Attesting Officer*     *Commissioner of Patents and Trademarks*